(12) United States Patent
Soliven (10) Patent No.: US 9,101,576 B2
(45) Date of Patent: *Aug. 11, 2015

(54) TREATMENT OF INFLAMMATORY DISEASES

(75) Inventor: Betty C. Soliven, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,590

(22) Filed: Aug. 6, 2012

(65) Prior Publication Data

US 2013/0017190 A1 Jan. 17, 2013

Related U.S. Application Data

(63) Continuation of application No. 12/377,736, filed as application No. PCT/US2007/018331 on Aug. 17, 2007, now Pat. No. 8,258,150.

(60) Provisional application No. 60/838,222, filed on Aug. 17, 2006.

(51) Int. Cl.

| | | |
|---|---|---|
| *A61K 31/137* | (2006.01) | |
| *A61K 31/133* | (2006.01) | |
| *A61K 31/138* | (2006.01) | |
| *A61K 31/4245* | (2006.01) | |
| *A61K 31/56* | (2006.01) | |
| *A61K 31/661* | (2006.01) | |
| *A61K 45/06* | (2006.01) | |

(52) U.S. Cl.
CPC ............. *A61K 31/133* (2013.01); *A61K 31/138* (2013.01); *A61K 31/4245* (2013.01); *A61K 31/56* (2013.01); *A61K 31/661* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,948,820 | A | 9/1999 | Fujita et al. | 514/653 |
| 6,004,565 | A | 12/1999 | Chiba et al. | 424/278.1 |
| 8,258,150 | B2 * | 9/2012 | Soliven | 514/291 |
| 2005/0090520 | A1 | 4/2005 | per Lindquist | 514/291 |
| 2006/0046979 | A1 | 3/2006 | Foster et al. | 514/79 |

FOREIGN PATENT DOCUMENTS

| | | |
|---|---|---|
| JP | 2006-503924 | 2/2006 |
| WO | WO 2004/028521 | 4/2004 |
| WO | WO 2005/025553 | 3/2005 |

OTHER PUBLICATIONS

Zou et al., INF-beta Suppresses Experimental Autoimmune Neuritis in Lewis Rats by Inhibiting the Migration of Inflammatory Cells Into Peripheral Nervous Tissue, 1999, Journal of Neuroscience Research 56(2):123-130.*

Pritchard et al., A Randomized Controlled Trial of Recombinant Interferon-beta 1A in Guillain-Barre Syndrome, 2003, Neurology 61:1282-1284.*

"FTY720, a novel once-daily oral medication, shows promising results in treatment of multiple sclerosis," *Novartis Media Release*, [online], retrieved from the world wide web at novartispharma.at/download/presse/intentationalFTY720%20-%ENGLISH%20%FINAL.pdf, accessed Jun. 28, 2006.

Bermingham et al., "Modification of representational difference analysis applied to the isolation of forskolin-regulated genes from Schwann cells," *J. Neurosci. Res.*, 63 (6): 516-524, 2001.

Bour-Jordan et al., "Distinct effector mechanisms in the development of autoimmune neuropathy versus diabetes in nonobese diabetic mice," *The Journal of Immunology*, 175:5649-5655, 2005.

Brinkmann et al., "The immune modulator FTY720 targets sphingosine 1-phosphate receptors," *The Journal of Biological Chemistry*, 277 (24): 21453-21457, 2002.

Coelho et al., "The immunomodulator FTY720 has a direct cytoprotective effect in oligodendrocyte progenitors," *J. Pharmacol. Exp. Ther.*, 323: 626-635, 2007.

Constantinescu et al., "Suppression of experimental autoimmune neuritis by phosphodiesterase inhibitor pentoxifylline," *J. Neurol. Sci.*, 143 (1-2): 14-18, 1996.

Coroneos et al., "Differential regulation of sphingomyelinase and ceramidase activities by growth factors and cytokines. Implications for cellular proliferation and differentiation," *J. Biol. Chem.*, 270 (40): 23305-23309, 1995.

Cuvillier et al., "Suppression of ceramide-mediated programmed cell death by sphingosine-1-phosphate," *Nature*, 381 (6585): 800-803, 1996.

Dorsam et al., "Transduction of multiple effects of sphingosine 1-phosphate (S1P) on T cell functions by the S1P1 G protein-coupled receptor," *J. Immunol.*, 171 (7): 3500-3507, 2003.

Extended European Search Report, issued in European Patent Application No. 11170326.0, mailed on Nov. 4, 2011.

Foster et al., "FTY720 rescue therapy in the dark agouti rat model of experimental autoimmune encelphaloymelitis: expression of central nervous system genes and reversal of blood brain barrier damage," *Brain Pathol.*, 19: 254-266, 2009.

Fujino et al., "Amelioration of experimental autoimmune encephalomyelitis in Lewis rats by FTY720 treatment," *J. Pharmacol. Exp. Ther.*, 305 (1): 700-77, 2003.

Graeler et al., "Cutting edge: suppression of T cell chemotaxis by sphingosine 1-phosphate," *J. Immunol.*, 169 (8): 4084-4087, 2002.

(Continued)

*Primary Examiner* — John Ulm
(74) *Attorney, Agent, or Firm* — Norton Rose Fulbright US LLP (57) ABSTRACT

The present invention relates generally to the field of inflammatory diseases of the peripheral nervous system. More particularly, it concerns methods for treating inflammatory diseases of the peripheral nervous system by modulating sphingosine-1-phosphate receptor activity. In one embodiment, the present invention provides a method of treating a subject with chronic inflammatory demyelinating polyneuropathy (CIDP) or other autoimmune neuropathies comprising administering to the subject an effective amount of FTY720.

10 Claims, 8 Drawing Sheets

(56) References Cited

OTHER PUBLICATIONS

Gräler and Goetzl, "The immunosuppressant FTY720 down-regulates sphingosine 1-phosphate G-protein-coupled receptors," *FASEB J.*, 18 (3): 1874-1878, 2004.

Gräler et al., "The sphingosine 1-phosphate receptor S1P4 regulates cell shape and motility via coupling to Gi and G12/13," *J. Cell. Biochem.*, 89 (3): 507-519, 2003.

Hadden et al., "Randomized trial of interferon [beta]-1a in chronic inflammatory demyelinating polyradiculoneuropathy," *Neurology*, 53(1):57-61, 1999.

Hida et al., "Ceramide inhibits inwardly rectifying K+ currents via a Ras- and Raf-1-dependent pathway in cultured oligodendrocytes," *J. Neurosci.*, 18 (21): 87121-8719, 1998.

Hughes et al., "Intramuscular interferon beta-1a in chronic inflammatory demyelinating polyradiculoneuropathy," *Neurology*, 74:651-657, 2010.

Idzko et al., "Sphingosine 1-phosphate induces chemotaxis of immature and modulates cytokine-release in mature human dendritic cells for emergence of Th2 immune responses," *FASEB J.*, 16 (6): 625-627, 2002.

Im et al., "Characterization of a novel sphingosine-1-phosphate receptor, Edg-8," *J. Biol. Chem.*, 275: 14281-14286, 2000.

International Preliminary Report on Patentability, issued in Int. App. No. PCT/US2007/018331, mailed Feb. 26, 2009.

International Search Report, issued in Int. App. No. PCT/US2007/018331, mailed Apr. 8, 2008.

Jaillard et al., "Edg8S1P5: an oligodendroglial receptor with dual function on process retraction and cell survival," *J. Neurosci.*, 25: 1459-1469, 2005.

Jin et al., "Sphingosine 1-phosphate is a novel inhibitor of T-cell proliferation," *Blood*, 101 (12): 4909-4915, 20003.

Jung et al., "Functional consequences of S1P receptor modulation in rat oligodendroglial lineage cells," *Glia.* 55: 1656-1667, 2007.

Karandikar et al., "Targeting the B7/CD28:CTLA-4 costimulatory system in CNS autoimmune disease," *J. Neuroimmunol.*, 89 (1-2): 10-18, 1998.

Kiefer et al., "Enhanced B7 costimulatory molecule expression in inflammatory human sural nerve biopsies," *J. Neurol. Neurosurg. Psychiat.*, 69 (3): 362-368, 2000.

Kim et al., "Fingolimod and related compounds in a spontaneous autoimmune polyneuropathy," *Journal of Neuroimmunology*, 214:93-100, 2009.

Kim et al., "Targeting of myelin protein zero in a spontaneous autoimmune polyneuropathy," *The Journal of Immunology*, 181:8753-5760, 2008.

Kim et al., "The beta 2-adrenergic agonist terbutaline suppresses experimental allergic neuritis in Lewis rats," *J. Neuroimmunol.*, 51 (2): 177-183, 1994.

Kiuchi et al., "Synthesis and immunosuppressive activity of 2-substituted 2-aminopropane-1,3-diols and 2-aminoethanols," *J. Med. Chem.*,43 (15): 2946-2961, 2000.

Kohno et al., "A novel immunomodulator, FTY720, prevents development of experimental autoimmune myasthenia gravis in C57BL/6 mice," *Biological & Pharmaceutical Bulletin*, 28 (4): 736-739, 2005.

Lee et al., "Lysophospholipid regulation of mononuclear phagocytes," *Biochim. Biohpys. Acta.*, 1582 (1-3): 175-177, 2002.

Li et al., "Lysophosphatidic acid promotes survival and differentiation of rat schwann cells," *J. Biol. Chem.*, 278 (11): 9585-9591, 2003.

Liu et al., "Differential regulation of sphingosine-1-phosphate- and VEGF-induced endothelial cell chemotaxis. Involvement of G(ialpha2)-linked Rho kinase activity," *Am. J. Respir. Cell. Mol. Biol.*, 24 (6): 711-719, 2001.

Louvet et al., "A novel myelin P0-specific T cell receptor transgenic mouse develops a fulminant autoimmune peripheral neuropathy," *J. Experimental Medicine*, 206:507-514, 2009.

Mandala et al., "Alteration of lymphocyte trafficking by sphingosine-1-phosphate receptor agonists," *Science*, 296 (5566): 346-349, 2002.

Matloubian et al., "Lymphocyte egress from thymus and peripheral lymphoid organs is dependent on S1P receptor 1 ," *Nature*, 427: (6972) 355-360, 2004.

Matsuda et al., "Caspase requirement for the apoptotic death of WR19L-induced by FTY720," *Transplant Proc.*, 30 (5): 2355-2357, 1998.

McGiffert and Chun, "Embryonic brain expression analysis of lysophospholipid receptor genes suggests roles for s1p(1) in neurogenesis and s1p(1-3) in angiogenesis," *FEBS Lett.*, 531 (1): 103-108, 2002.

Miron et al., "Cyclical and dose-dependent responses of adult human mature oligodendrocytes to fingolimod," *Am. J. Pathol.*, 173: 1143-1152, 2008.

Miron et al., "FTY720 modulates human oligodendroglial progenitor process extension and survival," *Ann. Neurol.*, 63: 61-71, 2008.

Murata et al., "Interaction of sphingosine 1-phosphate with plasma components, including lipoproteins, regulates the lipid receptor-mediated actions," *Biochem. J.*, 352 (3): 809-815, 2000.

Nagahara et al., "Evidence that FTY720 induces T cell apoptosis in vivo," *Immunopharmacology*, 48 (1): 75-85, 2000.

Nagano et al., "Cytokine-induced cell death in immortalized Schwann cells: roles of nitric oxide and cyclic AMP," *J. Neurochem.*, 77 (6): 1486-1495, 2001.

Notice of Allowance in U.S. Appl. No. 12/377,736, issued May 3, 2012.

Office Communication, issued in Japanese Patent Application No. 2009-524698, dated Aug. 27, 2012. (English translationg).

Office Communication, issued in Chinese Patent Application No. 200780034467.6, dated Feb. 24, 2011. (English translation).

Office Communication, issued in European Patent Application No. 07837041.8, mailed on Oct. 20, 2011.

Office Communication, issued in Russian Patent Application No. 2009109418, dated Apr. 11, 2011. (English translation).

Office Communication, issued in U.S. Appl. No. 12/377,736, dated Apr. 8, 2011.

Office Communication, issued in U.S. Appl. No. 12/377,736, dated Oct. 19, 2011.

Oyama et al., "Cytotoxic actions of FTY720, a novel immunosuppressant, on thymocytes and brain neurons dissociated from the rat," *Japan J. Pharmacol.*, 76 (4): 377-385, 1998.

Pinschewer et al., "FTY720 immunosuppression impairs effector T cell peripheral homing without affecting induction, expansion, and memory," *J. Immunol.*, 164 (11): 5761-5770, 2000.

Prineas and McLeod, "Chronic relapsing polyneuritis," *J. Neurol. Sci.*, 27 (4): 427-458, 1976.

Ropper, "Current treatments for CIDP," *Neurol.*, 60 (8 Supp. 3): S 16-S22, 2003.

Rosen et al., "Rapid induction of medullary thymocyte phenotypic maturation and egress inhibition by nanomolar sphingosine 1-phosphate receptor agonist," *PNAS USA.* 100 (19): 10907-10912, 2003.

Salomon et al., "Development of spontaneous autoimmune peripheral polyneuropathy in B7-2-deficient NOD mice," *J. Exp. Med.*, 194 (5): 677-684, 2001.

Sanna et al., "Enhancement of capillary leakage and restoration of lymphocyte egress by a chiral S1P1 antagonist in vivo," *Nat. Chem. Biol.*, 2(8):434-441, 2006.

Sato et al., "Sphingosine 1-phosphate induces expression of early growth response-1 and fibroblast growth factor-2 through mechanism involving extracellular signal-regulated kinase in astroglial cells," *Brain Res. Mol. Brain Res.*, 74 (1-2): 182-189, 1999.

Schaphorst et al., "Role of sphingosine-1 phosphate in the enhancement of endothelial barrier integrity by platelet-released products," *Am. J. Physiol. Lung Cell. Mol. Physiol.*, 285 (1): 258-267, 2003.

Schneider-Schaulies et al., "Down-regulation of myelin-associated glycoprotein on Schwann cells by interferon-gamma and tumor necrosis factor-alpha affects neurite outgrowth," *Neuron*, 7 (6): 995-1005, 1991.

Spiegel and Millstien, "Sphingolipid metabolites: members of a new class of lipid second messengers," *J. Membr. Biol.*, 146 (3): 225-237, 1995.

Spiegel and Milstien, "Sphingosine-1-phosphate: an enigmatic signalling lipid," *Molec. Cell. Biol.*, 4 (5): 397-440, 2003.

(56) References Cited

OTHER PUBLICATIONS

Suzuki et al., "Long-term graft acceptance in allografted rats and dogs by treatment with a novel immunosuppressant, FTY720," *Transplant Proc..*, 28 (3): 1375-1376, 1996.

Terai et al., "Edg-8 receptors are preferentially expressed in oligodendrocyte lineage cells of the rat CNS," *Neurosci.*, 116 (4): 1053-1062, 2003.

Toyka & Gold, "The pathogenesis of CIDP: rationale for treatment with immunomodulatory agents," *Neurology*, 60(Suppl. 3):S2-S7, 2003.

Vallat et al., "Interferon beta-1a as an investigational treatment for CIDP," *Neurology*, 60 (8 Supp. 3): S23-S28, 2003.

Weiner et al., "Regulation of schwann cell morphology and adhesion by receptor-mediated lysophosphatidic acid signaling," *J. Neurosci.*, 21 (18): 7069-7078, 2001.

Windh et al., "Differential coupling of the sphingosine 1-phosphate receptors Edg-1, Edg-3 and H1218/Edg-5 to the G(i), G(q), and G(12) families of hetcrotrimeric G proteins," *J. Biol. Chem.*, 274 (39): 27351-27358, 1999.

Xie et al., "Sphingosine-1-phosphate receptor agonism impairs the efficiency of the local immune response by altering trafficking of naive and antigen-activated CD4+ T cells," *J. Immunol.*, 170 (7): 3662-3670, 2003.

Yamagata et al., "Sphingosine 1-phosphate induces the production of glial cell line-derived neurotrophic factor and cellular proliferation in astrocytes," *Glia*, 41 (2): 199-206, 2003.

Zhang et al., "FTY780 ameliorates experimental allergic neuritis by inhibition of lymphocyte and monocyte infiltration into peripheral nerves," *Exp. Neurol.*, 240: 681-690, 2008.

Zhu et al., "CD28-B7 costimulation: a critical role for initiation and development of experimental autoimmune neuritis in C57BL/6 mice," *J. Neuroimmunol.*, 114 (1-2): 114-121, 2001.

Zhu et al., "Suppression of autoimmune neuritis in IFN-gamma receptor-deficient mice," *Exp. Neurol.*, 169 (2): 472-478, 2001.

Zondag et al., "Sphingosine 1-phosphate signalling through the G-protein-coupled receptor Edg-1," *Biochem. J.*, 330 (2): 605-609, 1998.

Gold et al., "Animal models for autoimmune demyelinating disorders of the nervous system", *Molecular Medicine Today* 6, 88-91, Feb. 2000.

Constantinescu et al., "Pathogenesis of Neuroimmunologic Diseases", *Immunologic Research*, 17:1&2, 217-227, 1998.

Chiba et al., "FTY720, a novel immunosuppressant, induces sequestration of circulating mature lymphocytes by acceleration of lymphocyte homing in rats. I. FTY720 selectively decreases the number of circulating mature lymphocytes by acceleration of lymphocyte homing," *J. Immunology*, 160 (10): 5037-5044, 1998.

\* cited by examiner

TREATMENT OF INFLAMMATORY DISEASES

This application is a continuation of U.S. patent application Ser. No. 12/377,736 filed Aug. 25, 2010 now U.S. Pat. No. 8,258,150, which is a national phase application under 35 U.S.C. §371 of International Application No. PCT/US2007/018331, filed Aug. 17, 2007, which claims the benefit of U.S. Provisional Application No. 60/838,222 filed Aug. 17, 2006. These applications are incorporated by reference.

The present application claims the benefit of U.S. Provisional Patent Application Ser. No. 60/838,222, filed Aug. 17, 2006, the entire disclosure of which is specifically incorporated herein by reference.

This invention was made with government support under grant number NS049014-02 awarded by the National Institutes of Health. The government has certain rights in the invention.

BACKGROUND OF THE INVENTION

A. Field of the Invention

The present invention relates generally to the field of inflammatory diseases of the peripheral nervous system. More particularly, it concerns methods for treating inflammatory diseases of the peripheral nervous system by modulating sphingosine-1-phosphate receptor activity.

B. Description of Related Art

The peripheral nervous system (PNS) is a common target of immune attack. Chronic inflammatory demyelinating polyneuropathy (CIDP) is sometimes referred to as the PNS counterpart of multiple sclerosis (MS), which affects the central nervous system, due to similarities between the two diseases in terms of course of illness (relapsing vs. progressive), presence of focal demyelination and varying degree of axonal loss, and immune-mediated pathophysiology. Inflammatory infiltrates in CIDP nerves consist primarily of T cells and macrophages, suggesting that T-cell mediated reaction towards myelin antigens is a probable cause of tissue damage in CIDP. Available therapies for CIDP, such as intravenous gammaglobulin, plasmapheresis and steroids, are effective in two-thirds of patients, but are associated with complications or failure to induce a long-lasting remission (Ropper, 2003). Therefore, there is a pressing need to develop new therapeutic methods and agents that can be used alone or in combination with existing treatment modalities.

SUMMARY OF THE INVENTION

The present invention provides therapies for inflammatory disorders and autoimmune disorders. In one embodiment, the present invention provides a method of treating a subject with an autoimmune disorder of the peripheral nervous system comprising administering to the subject an effective amount of a sphingosine 1-phosphate receptor modulator. In another embodiment, the present invention provides a method of alleviating a symptom of an autoimmune disorder of the peripheral nervous system in a subject comprising administering to the subject an effective amount of a sphingosine 1-phosphate receptor modulator. In a further embodiment, the present invention provides a method of prolonging time to relapse of an autoimmune disorder of the peripheral nervous system in a subject comprising administering to the subject an effective amount of a sphingosine 1-phosphate receptor modulator.

In another embodiment, the present invention provides a method of treating a subject with an autoimmune disorder of muscle comprising administering to the subject an effective amount of a sphingosine-1-phosphate receptor modulator, wherein the autoimmune disorder of the peripheral nervous system is treated. In another embodiment, the present invention provides a method of alleviating a symptom of an autoimmune disorder of muscle in a subject comprising administering to the subject an effective amount of a sphingosine 1-phosphate receptor modulator. In a further embodiment, the present invention provides a method of prolonging time to relapse of an autoimmune disorder of muscle in a subject comprising administering to the subject an effective amount of a sphingosine 1-phosphate receptor modulator.

In another embodiment, the present invention provides a method of treating a subject with an autoimmune disorder of a neuromuscular junction comprising administering to the subject an effective amount of a sphingosine-1-phosphate receptor modulator, wherein the autoimmune disorder of a neuromuscular junction is treated. In another embodiment, the present invention provides a method of alleviating a symptom of an autoimmune disorder of a neuromuscular junction in a subject comprising administering to the subject an effective amount of a sphingosine 1-phosphate receptor modulator. In a further embodiment, the present invention provides a method of prolonging time to relapse of an autoimmune disorder of a neuromuscular junction in a subject comprising administering to the subject an effective amount of a sphingosine 1-phosphate receptor modulator.

In one embodiment, a sphingosine 1-phosphate receptor modulator is used in the treatment of a peripheral nervous system disorder. In certain aspects, the peripheral nervous system disorder is Guillain-Barré syndrome (GBS), chronic inflammatory demyelinating polyneuropathy (CIDP), an antibody mediated neuropathy, or a vasculitic neuropathy. In some embodiments, a sphingosine 1-phosphate receptor modulator is used in the treatment of autoimmune conditions affecting the muscle (e.g. myositis) or neuromuscular junction (e.g. myasthenia).

Symptoms of inflammatory or autoimmune disorders of the peripheral nervous system include, for example, tingling or numbness (typically beginning in toes and fingers), weakness of the arms, weakness of the legs, loss of deep tendon reflexes (areflexia), fatigue, and abnormal sensations. Symptoms of inflammatory or autoimmune disorders of the muscle include, for example, muscle weakness, muscle atrophy, muscle pain, general fatigue, and dysphagia (difficulty swallowing). Symptoms of inflammatory or autoimmune disorders of the neuromuscular junction include, for example, muscle weakness, asymmetrical ptosis (a drooping of one or both eyelids), diplopia (double vision) due to weakness of the muscles that control eye movements, unstable or waddling gait, weakness in arms, hands, fingers, legs, and neck, a change in facial expression, dysphagia (difficulty in swallowing), shortness of breath, and dysarthria (impaired speech). One or more of these symptoms may be alleviated by the methods of the present invention. By the phrase "alleviating a symptom of an inflammatory disorder of the peripheral nervous system" it is meant that the symptom is made less severe or more bearable.

In certain aspects of the invention, the sphingosine 1-phosphate receptor modulator is FTY720, FTY720-P, AAL(R), AFD(R), or SEW2871. In some aspects of the invention, the sphingosine 1-phosphate receptor modulator is a down regulator of a sphingosine 1-phosphate receptor. In other aspects of the invention, the sphingosine 1-phosphate receptor modulator is an agonist of a sphingosine 1-phosphate receptor. The sphingosine 1-phosphate receptor may be, for example, a S1P1, S1P2, S1P3, S1P4, and/or S1P5 receptor.

The sphingosine-1-phosphate receptor modulator may be administered to the subject prior to the onset of symptoms of the autoimmune disorder of the peripheral nervous system, or it may be administered to the subject after the onset of symptoms of the autoimmune disorder of the peripheral nervous system. In certain aspects of the invention, the sphingosine-1-phosphate receptor modulator is administered to the subject during remission of symptoms of the autoimmune disorder of the peripheral nervous system. In certain embodiments of the invention, the sphingosine-1-phosphate receptor modulator is administered to the subject both prior to and after the onset of symptoms of the autoimmune disorder. The sphingosine-1-phosphate receptor modulator may be administered by any route known to those in the art. In certain embodiments, the sphingosine-1-phosphate receptor modulator is administered orally or by injection. For oral administration, the sphingosine-1-phosphate receptor modulator may be provided in any pharmaceutical composition suitable for oral administration, such as a liquid, capsule, or tablet. For injection, the sphingosine-1-phosphate receptor modulator may be provided in any pharmaceutical composition suitable for injection, such as in a syringable liquid. The injection may be, for example, intravenous, intra-arterial, intramuscular, or subcutaneous.

In certain aspects of the invention, the sphingosine-1-phosphate receptor modulator is administered on a daily, twice-daily, or three-times-daily basis. In some embodiments, the sphingosine-1-phosphate receptor modulator is administered about every 4 hours, 6 hours, 8 hours, 12 hours, 24 hours, 48 hours, or 72 hours. In certain aspects of the invention, the daily dosage of sphingosine-1-phosphate receptor modulator administered to a human subject is between about 0.1 mg to 20 mg, 0.5 mg to 10 mg, 0.5 mg to 5 mg, 1 mg to 5 mg, 1.25 mg to 5 mg, 1.5 mg to 3 mg, 0.1 mg to 1 mg, or any range derivable therein. In some aspects of the invention, the sphingosine-1-phosphate receptor modulator is administered every other day, every third day, every fourth day, every fifth day, weekly, or monthly. The practitioner responsible for administration of a composition of the present invention will be able to determine the appropriate dosage amount, route of administration, and frequency of administration by assessing physical and physiological factors of the subject such as body weight, gender, severity of condition, and previous or concurrent therapeutic interventions.

It is also contemplated that the sphingosine-1-phosphate receptor modulator may be administered in combination with a second therapeutic agent. For example, the sphingosine-1-phosphate receptor modulator may be administered in combination with an immunosuppresant (e.g., cyclosporin A, cyclosporin G, FK-506, ABT-281, ASM981, rapamycin, 40-O-(2-hydroxy)ethyl-rapamycin, corticosteroids. cyclophosphamide, azathioprine, methotrexate, leflunomide, mizoribine, mycophenolate mofetil, or 15-deoxyspergualine), a steroid (e.g., prednisone or hydrocortisone), an immunoglobulin, or type 1 interferon. The sphingosine-1-phosphate receptor modulator and the second agent can be administered simultaneously or consecutively. Where the sphingosine-1-phosphate receptor modulator and the second agent are administered simultaneously, they may be formulated into a single composition or in separate compositions.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 provides the chemical structures of sphingosine, sphingosine-1-phosphate, FTY720, FTY720-P, AAL(R), AFD(R), and SEW2871.

FIG. 2 provides examples of CMAPs from sciatic nerve stimulation in wild type and $B7-2^{-/-}$ NOD mice.

FIG. 4 shows the ceramide levels as a percentage of controls in SCs induced with TNF-α (100 g/ml)+IFN-γ (200 U/ml), L-NAME (NOS inhibitor), or TNF-α (100 g/ml)+IFN-γ (200 U/ml)+L-NAME. Cytokine induction was for 24 hours. The asterisk (*) indicates $p<0.0001$.

FIG. 5A shows the clinical scores for B7-2 deficient NOD mice at 7 months (pre-treatment) and 8 months (post-treatment) for mice administered vehicle (water), FTY720 at 0.3 mg/kg, or FTY720 at 1.0 mg/kg. The asterisk (*) indicates $p<0.0007$. In contrast, clinical scores of mice treated with FTY720 (1 mg/kg) did not become worse. At the end of the 4 week treatment, hindlimb and forelimb grip strength was measured with a grip strength meter (Columbus Instruments). FIG. 5B shows the results of the hindlimb and forelimb grip strength measurements for mice administered vehicle (water), FTY720 at 0.3 mg/kg, or FTY720 at 1.0 mg/kg. The asterisk (*) indicates $p<0.01$. Error bars represent SEM.

FIG. 6A shows examples of sciatic CMAPs. FIG. 6B shows a summary of the data collected from 12 nerves of vehicle-treated mice and 14 nerves of mice treated with FTY720 at 1.0 mg/kg. The asterisk (*) indicates $p<0.02$; double asterisk (**) indicates $p<0.01$.

DESCRIPTION OF ILLUSTRATIVE EMBODIMENTS

A. Pathogenesis of Chronic Inflammatory Demyelinating Polyneuropathy

Chronic inflammatory demyelinating polyneuropathy (CIDP) is an inflammatory disease of the peripheral nervous system (PNS). The course of illness can be relapsing or progressive, and is characterized by the presence of focal demyelination, varying degree of axonal loss, and immune-mediated pathophysiology. Inflammatory infiltrates in CIDP nerves consist primarily of T cells and macrophages, suggesting that T-cell mediated reaction towards myelin antigens is a probable cause of tissue damage in CIDP. However, the antigenic targets of aberrant T-cell responses remain unidentified. Current treatments for CIDP include corticosteroids such as prednisone, which may be used alone or in combination with immunosuppressant drugs; plasmapheresis; and intravenous immunoglobulin. Physiotherapy may improve muscle strength, function, and mobility, and minimize the shrinkage of muscles and tendons and distortions of the joints.

Complete activation of T cells requires signaling via costimulatory molecules, B7-1 and B7-2, in addition to antigen-specific signaling via T cell receptors. Antigen presentation in the presence of B7-1 causes T cell differentiation to a Th1 phenotype with expression of interleukin-2, IFN-γ, and TNF-α, whereas presentation in association with B7-2 induces a Th2 phenotype with predominant expression of IL-4 (Karandikar et al., 1998; Kuchroo et al., 1995). Consistent with the above concept, there is a preferential upregulation of B7-1 in CIDP nerves (Kiefer et al., 2000). Studies in CD28 knockout mice reveal that CD28 is required for the development of experimental allergic neuritis (EAN), an animal model for Guillain-Barré syndrome (GBS) (Zhu et al., 2001b). In NOD mice, diabetes can be prevented by treatment with anti-B7-2 antibody or by elimination of B7-2 expression, but these manipulations trigger a spontaneous autoimmune polyneuropathy (SAP), which mimics CIDP clinically, histologically, and electrophysiologically (Salomon et al., 2001). The progressive course in this model is distinct from that in EAN, which is usually monophasic with spontaneous recovery with only a few exceptions. In EAN, animals are immunized with peripheral myelin or purified myelin proteins such as P0, P2, PMP22, or MAG (Constantinescu et al., 1996; Kim et al., 1994; Stoll et al., 1993; Zhu et al., 2001b).

Activated lymphocytes migrate across the blood nerve barrier (BNB), which depends on the interaction between molecules on lymphocytes and adhesion molecules on endothelial cells. Once there is ample mononuclear infiltration, peripheral nerve injury and demyelination can occur by multiple mechanisms. Aside from elaborating cytotoxic compounds and cytokines such as TNF-α, macrophages may penetrate seemingly intact myelin sheaths and strip myelin from the axonal surface (Prineas and McLeod, 1976). Th1 cytokines such as TNF-α and IFN-γ act synergistically to decrease Schwann cell (SC) viability via iNOS induction and ceramide accumulation (Nagano at al., 2001). Others have found that these cytokines inhibit SC proliferation and down-regulate the expression of myelin-associated glycoprotein (Chandross et al., 1996; Schneider-Schaulies at al., 1991).

Schwann cells play a multifunctional role in inflammatory neuropathies, acting as antigen presenting cells, targets of immune attack, as well as a source of neurotrophic factors. These cells express S1P2 and S1P3 receptors; the latter is upregulated by an adenylate cyclase activator forskolin (Bermingham et al., 2001; Weiner at al., 2001). Agents that elevate cAMP are protective against EAN and decrease the susceptibility of SCs to cytokine-induced cell death (Kim at al., 1994; Nagano et al., 2001). The protective effect of cAMP may be mediated in part by regulating the expression of S1P receptors on SCs, and sphingolipid signaling may play an important role in SC survival and differentiation. Factors leading to the termination versus persistence of the immune response are not fully understood. FasL-expressing Schwann cells may contribute to the elimination of autoreactive T cells (Wohlleben et al., 2000). Remission is generally associated with increased production of IL-4, IL-10 and TGF-β.

B. Sphingolipid Signaling in Lymphocytes and Glial Cells

In many cell types, growth factors and cytokines have been shown to modulate the activity of enzymes involved in the control of the so-called ceramide/S1P rheostat, a critical determinant of the cellular outcome (Cuvillier at al., 1996; Spiegel and Milstien, 2003). Pro-inflammatory cytokines such as TNF-α and interleukin-1 activate sphingomyelinase, but not ceramidase, resulting in accumulation of ceramide, whereas PDGF and FGF upregulate ceramidase in addition to sphingomyelinase, leading to a decrease in ceramide and increase in sphingosine, which can then be converted to sphingosine 1-phosphate (S1P) (Coroneos et al., 1995).

Activated platelets, monocytes, and mast cells are known to secrete S1P, resulting in up to μM concentrations in plasma (Murata et al., 2000; Spiegel and Milstien, 1995). Hence, S1P can potentially function either as an intracellular messenger or as an extracellular ligand for G-protein-coupled receptors S1P1-S1P5 (formerly called Edg1, Edg5, Edg3, Edg6, and Edg8, respectively). S1P receptors are coupled to a variety of G proteins. For example, S1P1 couples to Gi/o and other members of the Gi family but not Gs, Gq, G12 or G13. Activation of S1P1 stimulates the phosphorylation of mitogen-activated protein kinase (MAPK), inhibits adenylate cyclase, and activates phospholipase C leading to a proliferative or migratory response (Windh et al., 1999; Zondag et al., 1998). In endothelial cells, where S1P1 and S1P3 genes were first identified, S1P stimulates DNA synthesis and cell migration and promotes endothelial barrier integrity (Liu et al., 2001; Schaphorst et al., 2003). S1P receptors are expressed by many cell types, but the predominant receptor subtypes differ from one cell type to another albeit with some overlap.

Of the S1P receptors expressed by T lymphocytes, S1P1 and S1P4 receptors predominate, but their expression is suppressed by TCR-dependent activation. S1P at low concentrations (≤0.1 µM) elicits T cell chemotaxis, while high concentrations are inhibitory (Graeler et al., 2002). Initial studies in transfectants revealed that the S1P1 receptor is the transducer of S1P-induced chemotaxis, but subsequent studies have revealed that overexpression of S1P4 in Jurkat T cells suffices to induce cell motility in the absence of exogenous S1P (Graler et al., 2003). In vitro studies reveal that S1P inhibits polyclonal T cell proliferation, but there is no consensus regarding its effect on cytokine secretion. S1P enhances secretion of IL-2 and IFN-γ by human T cells while it decreases the secretion of IFN-γ and IL-4 by murine CD4+ T cells without affecting IL-2 (Dorsam et al., 2003; Jin et al., 2003). Aside from lymphocytes, mouse macrophages and dendritic cells also express S1P receptors (S1P1, S1P2, S1P3 and S1P5). Treatment of mature dendritic cells with S1P is associated with the emergence of a Th2 immune response (Idzko et al., 2002; Lee et al., 2002). Hence the net outcome of S1P action on the polarization of an immune response (Th1 vs Th2) in vivo remains to be clarified.

S1P receptors are expressed in glial cells. It has been shown that exogenous S1P activates the ERK cascade and modulates $Ca^{2+}$ signals in oligodendrocytes (OLGs) (Hida et al., 1998). S1P induces the expression of growth factors such as glial cell line-derived neurotrophic factor in astrocytes (Sato at al., 1999; Yamagata et al., 2003). Cells of OLG lineage express predominantly S1P1, S1P5, and possibly S1P2, whereas Schwann cells express S1P2 and S1P3 receptors (Bermingham et al., 2001; Im et al., 2000; McGiffert and Chun; 2002; Terai et al., 2003; Weiner at al., 2001). Lysophosphatidic acid, which acts on other Edg receptors, has been shown to promote survival and differentiation of SCs as well as to regulate their morphology and adhesion (Li et al., 2003; Weiner et al., 2001).

C. Modulators of Sphingosine 1-Phosphate Receptors

Sphingosine1-phosphate (S1P) receptors are implicated in the regulation of lymphocyte trafficking. S1P receptors are expressed in several cell types involved in the pathogenesis of inflammatory diseases of the peripheral nervous system such as glial cells, macrophages, endothelial cells, and Schwann cells. The present invention provides methods for treating inflammatory diseases, such as inflammatory diseases of the peripheral nervous system, by modulating S1P receptor activity in patients.

FTY720 (2-amino-2-[2-(4-octylphenyl)ethyl]-1,3-propanediol) is an immunomodulatory agent that has been shown to be effective in transplant models. It acts by sequestering lymphocytes in lymphoid organs with concomitant peripheral blood lymphopenia and a decrease in T cell migration to target tissues (Chiba et al., 1998; Pinschewer et al., 2000; Xie et al., 2003). FTY720 shares structural similarity with sphingosine, which suggests that it acts via S1P receptors (Brinkmann et al., 2002; Suzuki et al., 1996). While FTY720 itself lacks T cell chemotactic activity, its phosphorylated form (FTY720-P) is a potent agonist of S1P receptors with the exception of S1P2, as detected by the [γ35]-GTPγS binding assay on transfected cells expressing individual S1P receptors (Brinkmann et al., 2002; Mandala at al., 2002). FTY720 is converted to FTY720-P extensively in viva (Brinkmann at al., 2002).

Downregulation or inactivation of S1P1 expression by FTY720 or its phosphorylated form provides an explanation for lymphocyte sequestration, similar to that observed in S1P1 null mice (Matloubian et al., 2004). Another proposed model is that FTY720 blocks lymphocyte exit via S1P1 agonist activity (Brinkmann et al., 2002; Mandala et al., 2002). At concentrations >3 µM, FTY720 elicits lymphocyte apoptosis (Matsuda at al., 1998; Oyama et al., 1998). FTY720 has been shown to be effective in experimental allergic encephalomyelitis (EAE) when treatment is initiated on the day of immunization with bovine spinal cord or MBP (Brinkmann et al., 2002; Fujino et al., 2003). FTY720 is currently being evaluated for the treatment of multiple sclerosis (MS), an inflammatory and neurodegenerative disorder of the central nervous system (CNS) ("FTY720, a novel once-daily oral medication, shows promising results in treatment of multiple sclerosis," *Novartis Media Release*, [online] retrieved from the world wide web at novartispharma.at/download/presse/international/FTY720%20-%20ENGLISH%20-%20FINAL.pdf. Accessed Jun. 28, 2006). However, a successful outcome in a CNS disorder does not always translate into a successful result in a PNS disorder. For example, interferon-β (IFN-β) is efficacious in decreasing MS attack frequency, but its place in the treatment of CIDP and other inflammatory neuropathies remains controversial. Improvement of CIDP patients receiving IFN-β was reported in 2 of 4 studies (Choudhary et al., 1995; Vallat et al., 2003; Kuntzer et al., 1999; Hadden et al., 1999).

Figure 1:
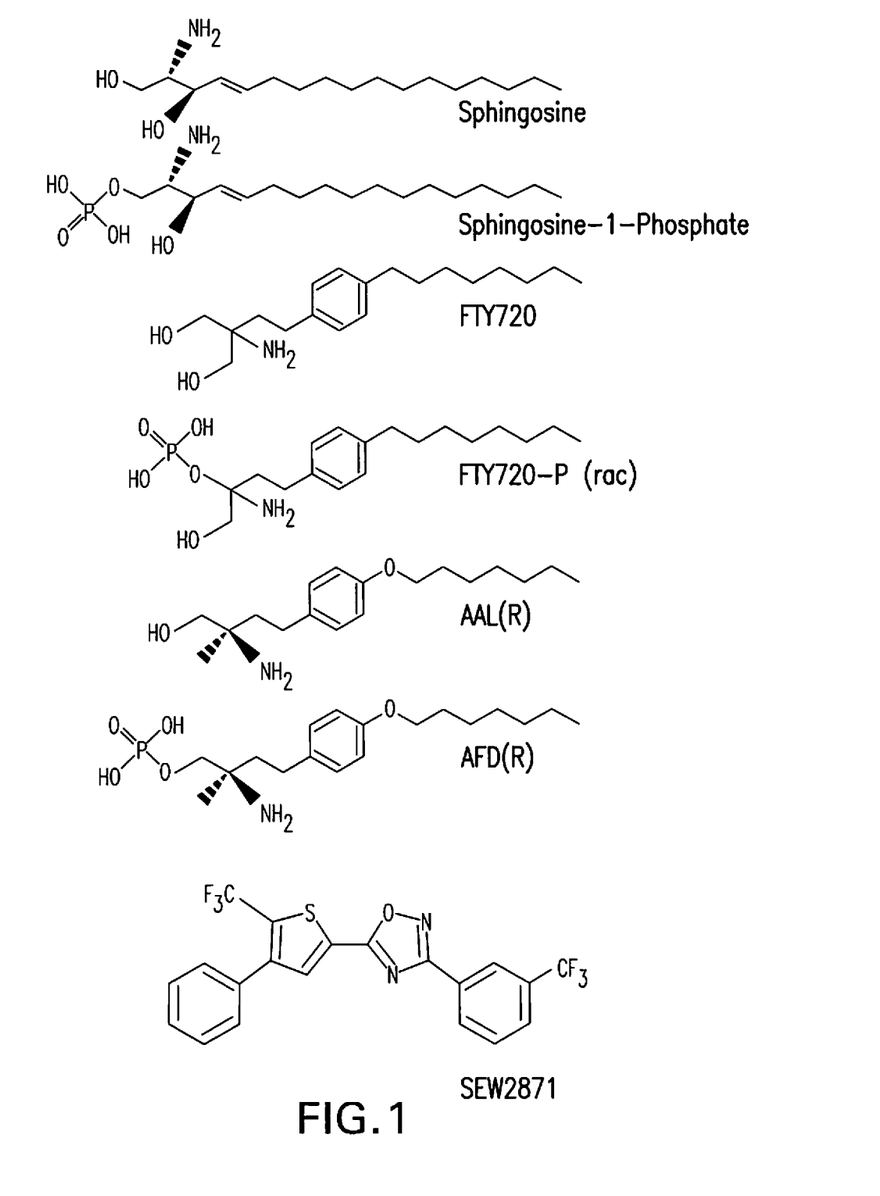
FIG. 1. Chemical structures of FTY720 and related compounds.

AAL(R) is a chiral methyl analog of FTY720 and AFD(R) is a phosphate ester of FTY720 (Kiuchi et al., 2000). AFD(R) acts as an agonist on four S1P receptors (S1P1, S1P3, S1P4, and S1P5) (Brinkmann et al., 2002). Recently, AAL(R) has been demonstrated to induce a rapid phenotypic change in medullary thymocytes resulting in downregulation of CD69 within 2 hours (Rosen et al., 2003). SEW2871 acts as an S1P1 agonist. These results indicate that FTY720 and related compounds exert pleiotropic actions on the immune system. The structures of sphingosine, sphingosine-1-phosphate, FTY720, FTY720-P, AAL(R), AFD(R), and SEW287 are provided in FIG. 1.

D. Pharmaceutical Compositions

Pharmaceutical compositions of the present invention comprise an effective amount of one or more modulators of S1P receptor activity dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one modulator of S1P receptor activity will be known to those of skill in the art in light of the present disclosure, and as exemplified by "Remington: The Science and Practice of Pharmacy," 21st Edition, 2005, incorporated herein by reference. Moreover, for human administration, it will be understood that preparations should meet sterility, pyrogenicity, general safety and purity standards as required by the FDA Office of Biological Standards.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g. paraffin), absorbents (e.g. kaolin clay, bentonite clay), drug stabilizers (e.g. sodium lauryl sulphate), gels, binders (e.g. syrup, acacia, gelatin, sorbitol, tragacanth, polyvinylpyrrolidinone, carboxy-methyl-cellulose, alginates), excipients (e.g. lactose, milk sugar, polyethylene glycol), disintegration agents (e.g. ager-ager, starch, lactose, calcium phosphate, calcium carbonate, alginic acid, sorbitol, glycine), wetting agents (e.g. cetyl alcohol, glycerol monostearate), lubricants, absorption accelerators (e.g. quaternary ammonium salts), edible oils (e.g. almond oil, coconut oil, oily esters or propylene glycol), sweetening agents, flavoring agents, coloring agents, fillers, (e.g. starch, lactose, sucrose, glucose, mannitol, slilcic acid), tabletting lubricants (e.g. magnesium stearate, starch, glucose, lactose, rice flower, chalk), carriers for inhalation (e.g. hydrocarbon propellants), buffering agents, or such like materials and combinations thereof, as would be known to one of ordinary skill in the art (see, for example, "Remington: The Science and Practice of Pharmacy," 21st Edition, 2005). Except insofar as any conventional carrier is incompatible with the active ingredient, its use in the therapeutic or pharmaceutical compositions is contemplated.

In any case, the composition may comprise various antioxidants to retard oxidation of one or more component. Examples of antioxidants includes ascorbic acid, cysteine hydrochloride, sodium sulfite, sodium bisulfate, sodium metabisulfite, ascorbyl palmitate, butylated hydroxytoluene, butylated hydroxyanisole, lecithin propyl gallate, and -tocopherol. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Pharmaceutically acceptable salts include the acid addition salts, e.g., those formed with the free amino groups of a proteinaceous composition or which are formed with inorganic acids such as, for example, hydrochloric, hydrobromic, or phosphoric acids; or such organic acids as acetic, oxalic, tartaric, benzoic, lactic, phosphorific, citric, maleaic, fumaric, succinic, napsylic, clavulanic, stearic, or mandelic acid. Salts formed with the free carboxyl groups can also be derived from inorganic bases such as for example, sodium, potassium, ammonium, calcium magnesium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

The present invention may be administered by any suitable method known to one of ordinary skill in the art (see, for example, "Remington: The Science and Practice of Pharmacy," 21st Edition, 2005). Routes of administration of pharmaceutical composition include, for example, oral, intradermal, subcutaneous, topical, by injection, infusion, continuous infusion, localized perfusion, bathing target cells directly, via a catheter, via a lavage, or by a combination of the forgoing.

The modulators of S1P receptor activity when administered orally may be in the form of tablets, capsules, sachets, vials, powders, granules, lozenges, reconstitutable powders, or liquid preparations. Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsions, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as a solvent is envisioned to result in extremely rapid penetration, delivering high concentrations of the active agents to a small area.

The actual dosage amount of a composition of the present invention administered to a patient can be determined by physical and physiological factors such as body weight, gender, severity of condition, the type of disease being treated, previous or concurrent therapeutic interventions, idiopathy of the patient, time of the administration, rate of excretion of the particular compound, and on the route of administration. The practitioner responsible for administration will, in any event, determine the concentration of active ingredient(s) in a composition and appropriate dose(s) for the individual subject.

In particular embodiments, prolonged absorption of an injectable composition can be brought about by the use in the compositions of agents delaying absorption, such as, for example, aluminum monostearate, gelatin or combinations thereof.

E. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Spontaneous Autoimmune Polyneuropathy (SAP) in B7.2 Deficient NOD Mouse

Figure 2:
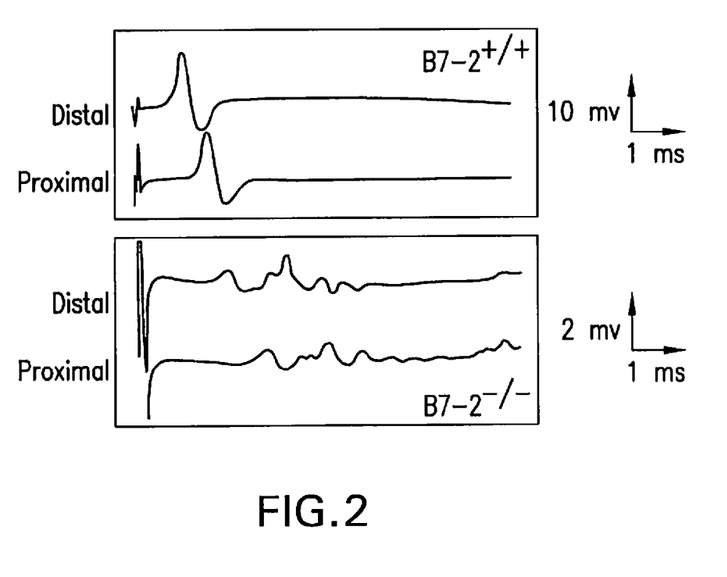
FIG. 2. Compound muscle action potentials (CMAPs).

In the course of an effort to examine the role of co-stimulatory signals in the NOD mouse, it was discovered that elimination of B7-2 expression prevented the development of hyperglycemia in these mice. However, these mice developed symmetrical hindlimb paresis beginning at 24 weeks of age (Salomon at al., 2001). Nerve conduction studies performed on sciatic nerves in vivo revealed a prolongation of distal latencies, marked slowing of conduction velocities, and dispersion of compound muscle action potentials (CMAPs), as shown in FIG. 2. Distal motor latency was 1.1±0.1 ms (n=8) in wt NOD and 2.7±0.4 ms in B7.2$^{-/-}$ NOD mice (p<0.005). Conduction velocity was 50.5±3.8 m/s in wt NOD, and 17.9±3.2 m/s in B7.2$^{-/-}$ NOD mice (p<0.00001). CMAP amplitude was 10.8±1.5 mV in wt NOD and 3.0±0.6 mV in B7.2$^{-/-}$ NOD mice (p<0.005). Partial conduction block, defined as 30% decline in amplitude with proximal versus distal stimulation, was observed in some, but not all, animals, probably related to the limited number of nerves studied. These electrophysiologic findings are classical for a demyelinating process with superimposed axonal loss.

Figure 3:
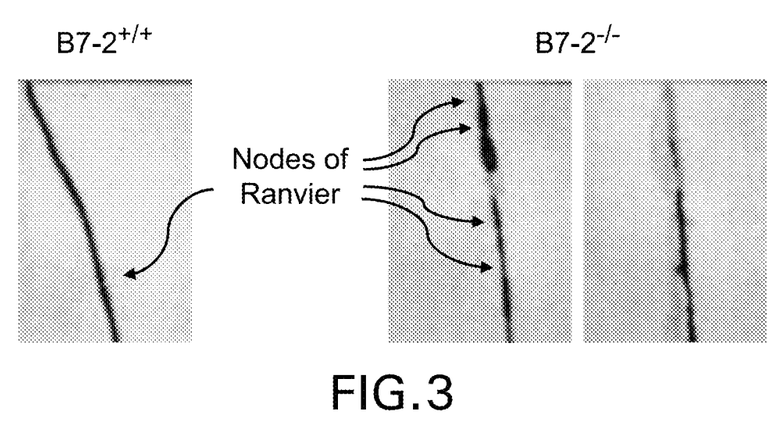
FIG. 3. Teased fiber preparations from sciatic nerves. Teased fiber preparations showed segmental demyelination and shortened internodes with irregular thickness of myelin sheaths in $B7-2^{-/-}$ NOD mice as compared to wild type NOD mice. Nodes of Ranvier are indicated with arrows.

Histologic evaluation revealed the presence of inflammatory infiltrates in the dorsal root ganglia (DRG) and sciatic nerves, but not in the CNS of B7-2$^{-/-}$ NOD mice. There was a significant loss of large diameter axons and evidence of thinly myelinated fibers on sciatic nerve sections. Teased fiber preparation showed segmental demyelination and shortened internodes with irregular thickness of myelin sheaths consistent with ongoing myelin repair (FIG. 3). That some remyelination occurs points to the potential reversibility of the process. Spontaneous autoimmune polyneuropathy (SAP) was induced in NOD-SCID mice by CD4+ T cells isolated from affected animals, but not in passive transfer studies using sera from affected animals. These studies demonstrate that the B7-2 deficient NOD mouse constitutes the first model of a spontaneous autoimmune neuropathy resembling the human disease CIDP; and that autoimmune-prone individuals have immune dysfunction that can manifest as distinct disease entities depending on the co-stimulatory milieu.

Example 2

Figure 4:
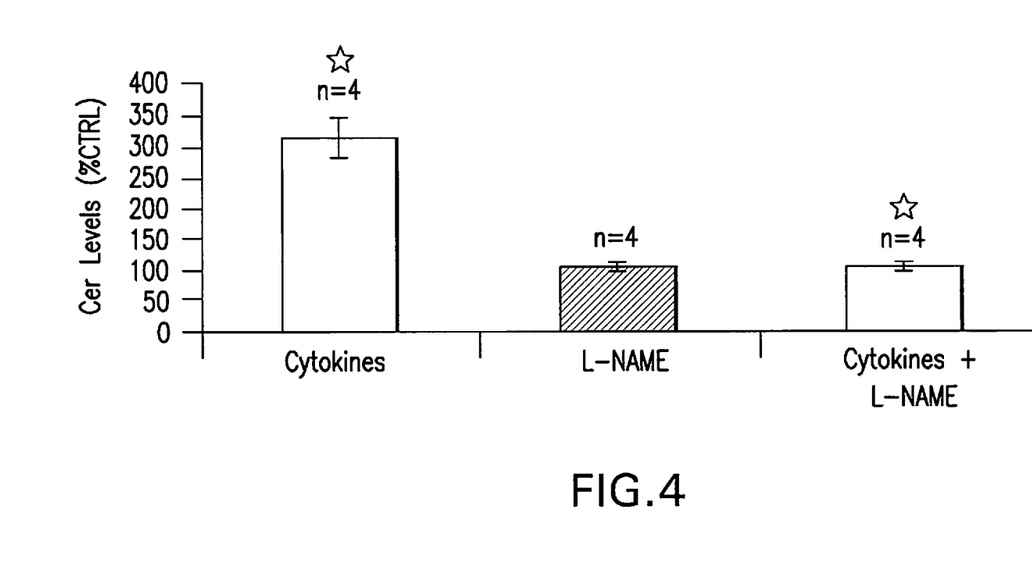
FIG. 4. Cytokine-induced ceramide accumulation in Schwann cells (SCs). TNF-α and IFN-γ acted synergistically to decrease cell viability via NOS induction and ceramide accumulation in immortalized SCs.

Synergistic Effect of Pro-Inflammatory Cytokines on SCs and Dorsal Root Ganglia (DRG)-SC Co-Cultures TNF-α and IFN-γ (labeled as cytokines) acted synergistically to decrease cell viability via NOS induction and ceramide accumulation in immortalized SCs (FIG. 4) (Nagano et al., 2001). Neither cytokine alone induced cell death. These cytokines also exerted a synergistic inhibitory action on myelination in neonatal DRG-SC co-cultures, which is evident after 3 days of treatment. No effect on myelination was observed with IFN-γ at 50-300 U/ml or low concentrations of TNF-α (10 ng/ml), though a modest inhibitory action was observed at 100 ng/ml of TNF-α. Cytokine-induced cell death affecting SCs and neurons was observed in co-cultures treated for 7 days.

Example 3

Effect of FTY720 on the Severity of SAP in B7-2 Deficient NOD Mice

FTY720 has been shown to inhibit lymphocyte emigration from lymphoid organs, and its phosphorylated form has been shown to be a potent agonist at four S1P receptors (Brinkmann et al., 2002; Grater and Goetzl, 2004; Matloubian et al., 2004). Recent studies suggest that the effect of these drugs in vivo may be due to downregulation of S1P receptors by FTY720 or its phosphorylated form (Brinkmann et al., 2002; Graler and Goetzl, 2004; Matloubian et al., 2004). The main consequence of these agents is lymphocyte sequestration in secondary lymphoid organs, although apoptosis was observed at higher concentrations (Brinkmann et at, 2002; Mandala et al., 2002; Nagahara et al., 2000). Oral administration of FTY720 prevents EAE when given at the time of immunization (Brinkmann et al., 2002; Fujino et al., 2003). However, it was previously unclear whether FTY720 or its chiral analog AAL(R) would be effective when administered after disease onset.

Given its resemblance to CIDP, the B7-2 deficient NOD mouse offers a unique opportunity to study agents that may halt disease progression or enhance recovery in autoimmune neuropathies. In this model of spontaneous autoimmune neuropathy, onset of symptoms occurred between 24 and 28 weeks. Left untreated, mice will deteriorate to the point of tetraparesis by 32 wks.

Female B7-2 deficient NOD mice were used since they are more prone to develop SAP than their male counterparts (Salomon et al., supra). The mice were 7 months of age at the start of the study. Animals were given FTY720 (aqueous solution) at doses of 0.3 mg/kg or 1 mg/kg or vehicle alone by oral gavage once daily for 1 month. The concentrations were chosen based on dose-response studies with regard to the depletion of peripheral lymphocytes, and data from EAE studies in rats (Brinkmann et al., 2002; Fujino et al., 2003).

Figure 5A:
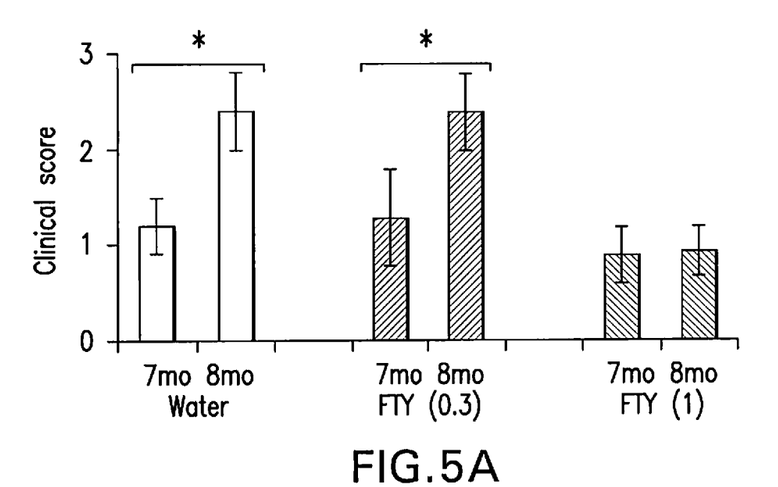
FIGS. 5A and 5B. Effect of FTY720 on clinical scores and grip strength of B7-2 deficient NOD mice. Animals were divided into 3 groups: (1) water (n=11); (2) FTY720 at 0.3 mg/kg (n=5); and (3) FTY720 at 1.0 mg/kg (n=10). Daily treatment was initiated at 7 months of age and continued for 4 weeks.
Figure 5B:
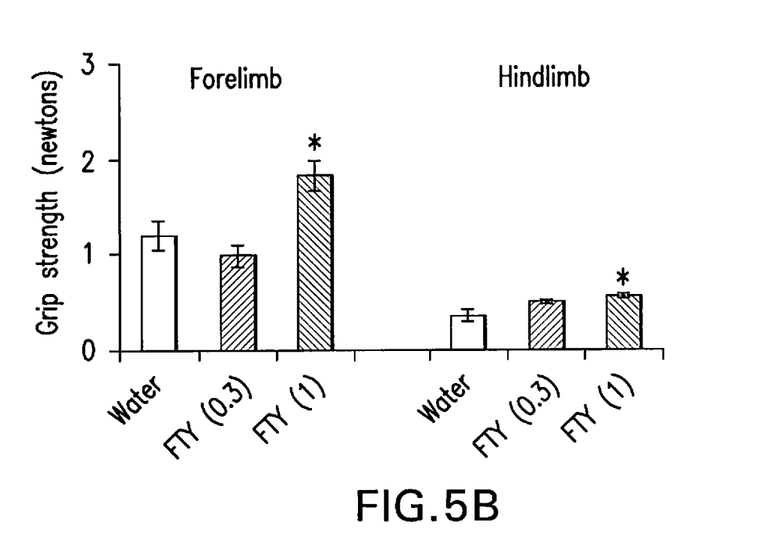

To determine the effect of FTY720 on clinical scores and grip strength of B7-2 deficient NOD mice, both qualitative and quantitative assessment was performed by blinded lab personnel. For qualitative assessment, a nominal scale (with 0 as normal and 5 as death) described by other investigators (Zhu et al., 2001a) was used. For quantitative assessment, hindlimb and forelimb strength was measured with a grip strength meter (Columbus Instruments). The animals treated for 1 month with 1 mg/kg FTY720 (n=10) exhibited less weakness qualitatively and quantitatively greater grip strength when compared to vehicle-treated animals (n=11) or animals treated with only 0.3 mg/kg FTY720 (n=5) (FIGS. 5A and 5B). The difference in clinical score between water-treated mice at 7 months and at 8 months was statistically significant, with a p value of less than 0.0007 (FIG. 5a). Likewise, the difference in clinical score between mice treated with 0.3 mg/kg FTY720 at 7 months and at 8 months was statistically significant, with a p value of less than 0.03. In contrast to vehicle-treated mice and mice treated with 0.3 mg/kg FTY720, clinical scores of mice treated with 1.0 mg/kg FTY720 did not increase between month 7 and month 8. Similar results were observed when forelimb and hindlimb strength was assessed quantitatively. Mice treated with 1.0 mg/kg FTY720 exhibited increased grip strength as compared to mice treated with vehicle or with 0.3 mg/kg FTY720 (FIG. 5B). These results indicate that FTY720 may be beneficial even when given after the onset of symptoms.

The effectiveness of FTY720 was also monitored by the induction of peripheral blood lymphopenia. The peripheral blood lymphocyte count was decreased to 50-60% of vehicle-treated ones by FTY720 (0.3 mg/kg) (n=4) and to 25-30% by FTY720 (1 mg/kg) (n=3).

Figure 6A:
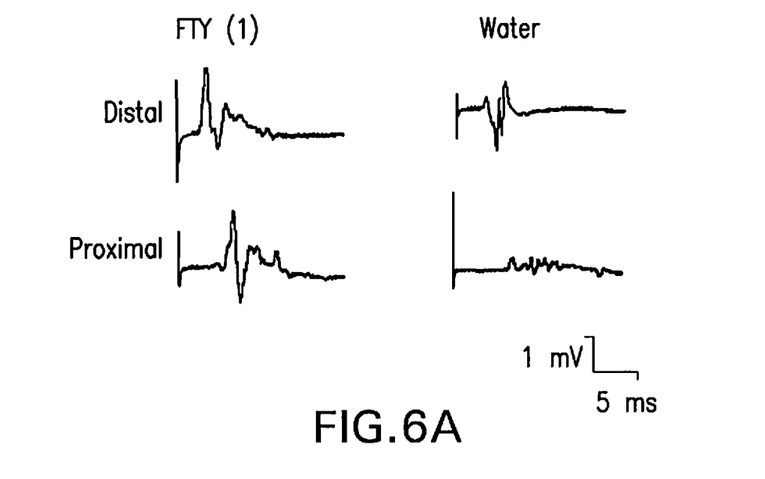
FIGS. 6A and 6B. Effect of FTY720 on distal latency, conduction velocity, and amplitude of sciatic compound muscle action potentials in B7-2 deficient NOD mice. Electrophysiological studies were performed to assess sciatic nerve function on mice treated with FTY720 at 1.0 mg/kg or with vehicle (water). Distal latency (DL), conduction velocity (CV), and sciatic compound muscle action potentials (CMAPs) were assessed. This figure illustrates that mice treated with FTY720 at 1.0 mg/kg demonstrated improved DL and CV as compared to vehicle-treated mice, but did not demonstrate improved amplitude of sciatic CMAPs.
Figure 6B:
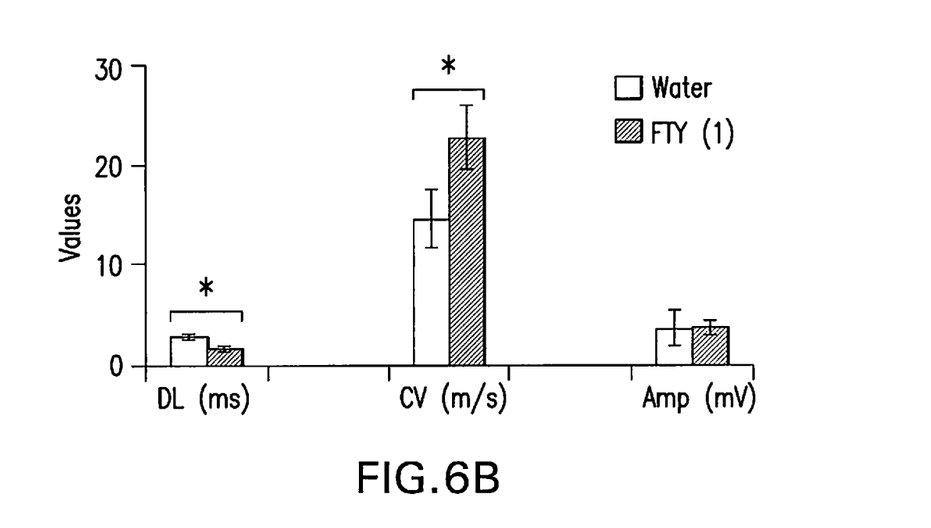

Electrophysiological studies were performed to assess the effect of FTY720 on sciatic nerve function in vivo in a subset of the study animals. Mice treated with 1.0 mg/kg FTY720 demonstrated improved distal latency (DL) and conduction velocity (CV) as compared to water-treated control mice, but did not demonstrate improved amplitude of sciatic compound muscle action potentials (CMAPs) (Table 1). FIG. 6 likewise illustrates that FTY720 treatment improves DL and CV (FIG. 6B, showing a summary of the results from experiments performed on 12 nerves from 6 water-treated mice and 14 nerves from 7 FTY720-treated mice) but not the amplitude of sciatic CMAPs (FIG. 6A).

TABLE 1

|  | Vehicle | FTY720 (1 mg/kg) |
|---|---|---|
| Distal Latency (ms) | 2.59 ± 0.3 | 1.58 ± 0.3* |
| Conduction Velocity (m/s) | 14.7 ± 3.0 | 22.8 ± 3.2** |
| Amplitude (mV) | 3.75 ± 1.8 | 3.8 ± 0.7 |

(*p < 0.02;
**p < 0.01)

Figure 7:
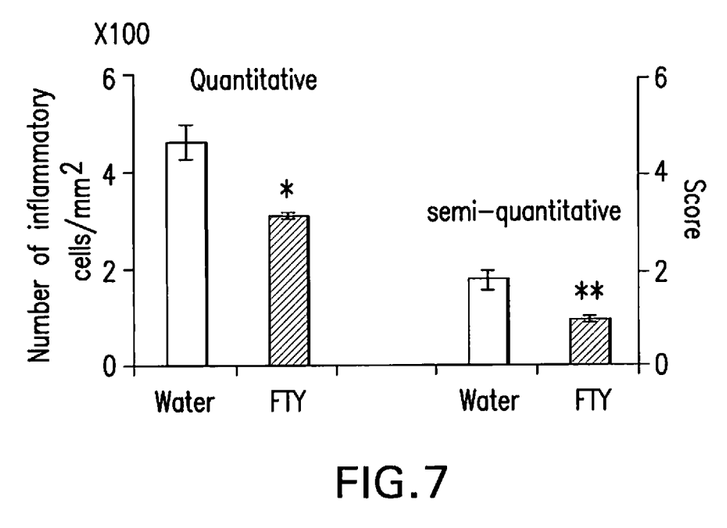
FIG. 7. Effect of FTY720 on inflammatory cell infiltration in sciatic nerve sections of B7-2 deficient NOD mice. Histological evaluation was performed on B7-2 deficient NOD mice treated with vehicle (water, n=6) or with FTY720 at 1.0 mg/kg (n=7). Inflammatory cell infiltration was measured by a quantitative method and by a semi-quantitative method. This figure demonstrates that inflammatory cell infiltration was decreased in sciatic nerve sections from FTY720-treated mice as compared to those from vehicle-treated mice. The asterisk (*) indicates $p<0.02$. The double asterisk (**) indicates $p<0.003$.

To further evaluate the effect of FTY720 on B7-2 deficient NOD mice, histological evaluation was performed to assess inflammatory cell infiltration. Using either the quantitative or semi-quantitative method, mice treated with 1.0 mg/kg FTY720 (n=7) exhibited decreased inflammatory cell infiltration as compared to mice treated with water (n=6) (FIG. 7). These observed differences were statistically significant with a p value of less than 0.02 when comparing water-treated mice to FTY720-treated mice using the quantitative method and a p value of less than 0.003 when making the comparison using the semi-quantitative method. For quantitative method, tissue areas were measured by image analysis and the number of inflammatory cells counted at ×20 magnification. The results were averaged and expressed as cells per $mm^2$ tissue section. For semi-quantitative method, inflammation was graded as: 1, a few scattered mononuclear inflammatory cells often subperineurial; 2, perivenular cuffing with mononuclear inflammatory cells (one or two foci); 3, extensive multifocal perivenular cuffing and widespread endoneurial inflammation.

Figure 8:
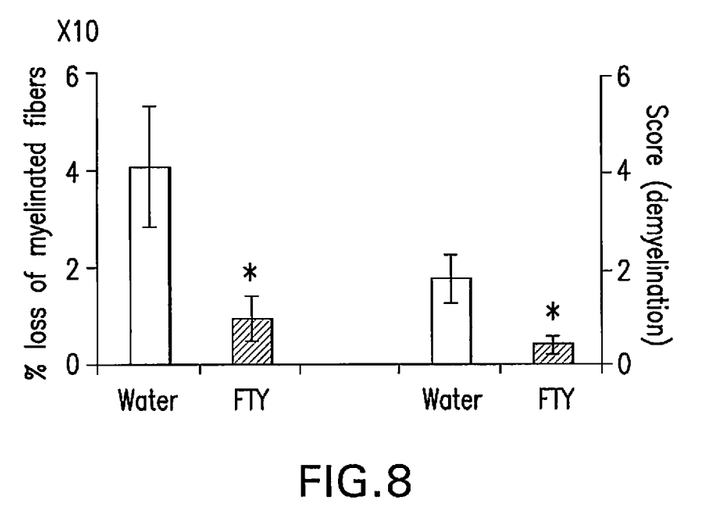
FIG. 8. Effect of FTY720 on demyelination and loss of myelinated fibers in B7-2 deficient NOD mice. Epon sections from B7-2 deficient NOD mice treated with vehicle (water, n=6) or with FTY720 at 1.0 mg/kg (n=7) were analyzed. Loss of myelinated fibers was measured by a quantitative method, and demyelination was measured by a semi-quantitative method. This figure demonstrates that demyelination and loss of myelinated fibers were attenuated in FTY720-treated mice as compared to vehicle-treated mice. The asterisk (*) indicates $p<0.015$.

FTY720 treatment also prevented demyelination and loss of myelinated fibers. Epon sections were prepared from vehicle-treated mice (n=6) and mice treated with 1.0 mg/kg FTY720 (n=7). FTY720-treated mice exhibited a decrease in the percentage of myelinated fibers lost and an increase in demyelination (FIG. 8). These differences were statistically different with a p value of less than 0.015. The percentage of loss of myelinated fibers in epon sections was assessed by a blinded observer using a grid. Demyelination was graded as follows: 1, isolated demyelinated axons perivascular or scattered; 2, many foci of perivascular demyelination; 3, extensive demyelination, perivascular and confluent.

Example 4

Investigating the Effect of FTY720 on Permeability of the Blood Nerve Barrier

Further experiments will determine whether FTY720 and related compounds, such as the S1P1 agonist SEW2871, can attenuate the disruption of the blood nerve barrier (BNB) when given after disease onset. To investigate the effect of FTY720 on permeability of the BNB, Evans blue (EBA) is injected intravenously in to B7-2 deficient NOD mice 1 hour prior to sacrifice. Vehicle-treated mice are compared to mice on day 1 of FTY720 treatment and on day 3 of FTY720 treatment. Confocal images of EBA with DIC imaging of longitudinal sciatic nerve sections are taken using similar conditions (e.g., same lens, laser power, pinhole size, etc.). If the EBA leakage in nerve tissues is attenuated by FTY720, this result will indicate that the therapeutic effect of FTY720 is mediated at least in part by alleviating disruption of the BNB. Negative results (I.e. no effect on the ability of EBA to cross the BNB) would imply that the ability of FTY720 to decrease inflammatory infiltration in sciatic nerve sections in SAP mice results from a decrease in lymphocyte migration to the target organs rather than a predominant action on S1P1 and/or S1P3 receptors expressed by endothelial cells.

Further experiments will also determine whether, in this mouse model, the immunoreactivity of splenocytes towards putative antigens is altered by FTY720 and related compounds. Splenocytes will be isolated from SAP mice treated with vehicle, FTY720, or FTY720-related compounds. Splenocyte proliferation is monitored by incorporation of thymidine (e.g. $^3$H-thymidine assay). Cytokine production in response to P0 protein peptide (180-199) (10-20 µg/ml), P2 protein peptide (57-81) (10-20 µg/ml), purified PNS myelin (100 µg/ml), and SC lysate (100 µg/ml) will also be assessed. A decrease in splenocyte proliferation and cytokine production would indicate that T cell activation is diminished in response to FTY720 and related compounds. This result would indicate that these compounds can act at both the early (priming) and late (effector) phases of the disease.

Example 5

Investigating the Role of S1P Receptors in Schwann Cells (SCs)

Purified SCs from neonatal rat sciatic nerves are treated with TNF-α (100 ng/ml)+IFN-γ (200 U/ml) for 48 to 72 hrs in serum-free conditions with or without FTY720-P (0.01-1 µM). The stated TNF-α and IFN-γ dosages are based on previous studies (Nagano et al., 2001). To determine if FTY720-P can decrease SC death, the level of cellular apoptosis is assayed following nuclear staining via propidium iodide and by the trypan blue assay. If FTY720-P decreases SC death, siRNA methods are used to determine which S1P receptor subtype mediates this effect. This approach may also be employed to determine if S1P agonists other than FTY720-P, such as S1P or SEW2871, can inhibit SC death.

In the event that FTY720-P or other S1P receptor agonists inhibit SC death, additional experiments are performed to examine the effect of FTY720-P and other S1P receptor agonists on the phosphorylation of ERK1/2 and Akt, which are signaling molecules linked to cell survival and proliferation. If no effect on survival, proliferation and phosphorylation assays is observed, this result would imply, that S1P receptors are not critical for survival, differentiation, or myelination of SCs. Positive results from the above studies would indicate that S1P receptors may serve as potential targets for glioprotective agents.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bermingham et al., *J. Neurosci. Res.*, 63:516-524, 2001.
Brinkman et al., *J. Biol. Chem.*, 277:21453-21457, 2002.
Chandross et al., *Molec. Cell Neurosci.*, 7:479-500, 1996.
Chiba et al., *J. Immunol.*, 160:5037-5044, 1998.
Choudhary et al., *J. Neurol.*, 242:252-253, 1995.
Constantinescu et al., *J. Neurol. Sci.*, 143:14-18, 1996.
Coroneos et al., *J. Biol. Chem.*, 270:23305-23309, 1995.
Cuvillier et al., *Nature*, 381:800-803, 1996.
Dorsam el al., *J. Immunol.*, 171:3500-3507, 2003.
Fujino et al., *J. Pharmacol. Exp. Ther.*, 305:70-77, 2003.
Graeler et al., *J. Immunol.*, 169:4084-4087, 2002.
Graler et al., *J. Cell Biochem.*, 89:507-519, 2003.
Grater and Goetzl, *FASEB J.*, 16:1874-1878, 2004.
Hadden et al., *Neurology*, 53:57-61, 1999.
Hida et al., *J. Neurosci.*, 18:8712-8719, 1998.
Idzko et al., *FASEB J.*, 16:625-627, 2002.
Jin et al., *Blood*, 101:4909-4915, 2003.
Karandikar et al., *J. Neuroimmunol.*, 89:10-18, 1998.
Kiefer et al., *J. Neurol. Neurosurg. Psychiat.*, 69:362-368, 2000.
Kim et al., *J. Neuroimmunol.*, 51:177-183, 1994.
Kiuchi et al., *J. Med. Chem.*, 43:2946-2961, 2000.
Kuchroo et al., *Cell*, 80:707-718, 1995.
Kuntzer et al., *Neurology*, 53:1364-1365, 1999.
Lee et al., *Biochim. Biophys. Acta*, 1582:175-177, 2002.
Li et al., *J. Biol. Chem.*, 278:9585-9591, 2003.
Liu et al., *Am. J. Respir. Cell Mol. Biol.*, 24:711-719, 2001.
Mandala et al., *Science*, 296:346-349, 2002.
Matloubian et al., *Nature*, 427:355-360, 2004.
Matsuda et al., *Transplant Proc.*, 30:2355-2357, 1998.
McGiffert and Chun, *FEBS Lett.*, 531(1):103-108, 2002.
Murata et al., *Biochem. J.*, 352(3):809-815, 2000.
Nagahara et al., *Immunopharmacology*, 48:75-85, 2000.
Nagano et al., *J. Neurochem.*, 77:1486-1495, 2001.
*Novartis Media Release*, "FTY720, a novel once-daily oral medication, shows promising results in treatment of multiple sclerosis," [online] retrieved from http://www.novartispharma.at/download/presse/international/FTY720%20-%20ENGLISH%20-%20FINAL.pdf.
Oyama et al., *Jpn. J. Pharmacol.*, 76:377-385, 1998.
Pinschewer et al., *J. Immunol.*, 164:5761-5770, 2000.
Prineas and McLeod, *J. Neurol. Sci.* 27:427-458, 1976.
Remington's Science and Practice of Pharmacy, 21$^{st}$ Ed., Mack Printing Company, 2005.
Ropper, *Neurol.*, 60:S16-S22, 2003.
Rosen et al., *Proc. Natl. Acad. Sci. USA*, 100:10907-10912, 2003.
Salomon et al., *J. Exp. Med.*, 194:677-684, 2001.
Sato et al., *Brain Res. Mol. Brain Res.*, 74:182-189, 1999.
Schaphorst et al., *Am. J. Physiol. Lung Cell Mol. Physiol.*, 285:258-267, 2003.
Schneider-Schaulies et al., *Neuron.*, 7:995-1005, 1991.
Spiegel and Milstien, *J. Membr. Biol.*, 146:225-237, 1595.
Spiegel and Milstien, *Molec. Cell Biol.*, 4:397-40, 2003.
Stoll et al., *J. Neuroimmunol.*, 45:175-182, 1993.
Suzuki et al., *Transplant Proc.*, 28:1375-1376, 1996.
Terai et at., *Neurosci.*, 116:1053-1062, 2003.
Vallat et al., *Neurology*, 60:S23-28, 2003.
Weiner et al., *J. Neurosci.*, 21:7069-7078, 2001.
Windh et al., *J. Biological Chem.*, 274:27351-27358, 1999.
Wohlleben et al., *Glia*, 30:373-381, 2000.
Xie et al., *J. Immunol.*, 170:3662-3670, 2003.
Yamagata et al., *Glia*, 41:199-206, 2003.
Zhu et al., *Exp. Neurol.*, 169:472-478, 2001a.
Zhu et al., *J. Neuroimmunol.*, 114:114-121, 2001b.
Zondag et al., *Biochem. J.*, 330(2):605-609, 1998.

The invention claimed is:

1. A method of inhibiting demyelination of the peripheral nervous system in a subject in need thereof, comprising administering to the subject an effective amount of a sphingosine-1-phosphate receptor modulator, wherein the sphingosine 1-phosphate receptor modulator is FTY720 or FTY720-P.

2. The method of claim 1, wherein the sphingosine 1-phosphate receptor modulator is FTY720.

3. The method of claim 1, wherein the sphingosine 1-phosphate receptor modulator is FTY720-P.

4. The method of claim 1, wherein the sphingosine 1-phosphate receptor modulator is administered to the subject prior to the onset of symptoms of autoimmune demyelination of the peripheral nervous system.

5. The method of claim 1, wherein the sphingosine 1-phosphate receptor modulator is administered to the subject after the onset of symptoms of autoimmune demyelination of the peripheral nervous system.

6. The method of claim 1, wherein the sphingosine 1-phosphate receptor modulator is administered orally.

7. The method of claim 1, further comprising administering to the subject an effective amount of an immunosuppressant.

8. The method of claim 1, further comprising administering to the subject an effective amount of a corticosteroid.

9. The method of claim 1, further comprising administering to the subject an effective amount of an immunoglobulin.

10. The method of claim 1, wherein autoimmune demyelination of the peripheral nervous system is inhibited.

* * * * *